US007485155B2

(12) United States Patent
Lalleman et al.

(10) Patent No.: US 7,485,155 B2
(45) Date of Patent: Feb. 3, 2009

(54) PROCESS FOR WASHING COLORED KERATINOUS FIBERS WITH A COMPOSITION COMPRISING AT LEAST ONE NONIONIC SURFACTANT AND METHOD FOR PROTECTING THE COLOR

(75) Inventors: Boris Lalleman, Paris (FR); Leïla Hercouet, Neully Plaisance (FR)

(73) Assignee: L'Oreal S.A., Paris (FR)

( * ) Notice: Subject to any disclaimer, the term of this patent is extended or adjusted under 35 U.S.C. 154(b) by 374 days.

(21) Appl. No.: 11/315,279

(22) Filed: Dec. 23, 2005

(65) Prior Publication Data

US 2006/0156478 A1 Jul. 20, 2006

Related U.S. Application Data

(60) Provisional application No. 60/645,068, filed on Jan. 21, 2005.

(30) Foreign Application Priority Data

Dec. 23, 2004 (FR) .................................. 04 53186

(51) Int. Cl.
*A61Q 5/10* (2006.01)
(52) U.S. Cl. ...................... 8/405; 8/406; 8/407; 8/410; 8/411; 8/435; 8/552; 132/202; 132/208
(58) Field of Classification Search .................. 8/406, 8/405, 407, 410, 411, 435, 552; 424/401, 424/70.19; 132/202, 208
See application file for complete search history.

(56) References Cited

U.S. PATENT DOCUMENTS

| 2,528,378 | A | | 10/1950 | Mannheimer |
| 2,781,354 | A | | 2/1957 | Mannheimer |
| RE30,199 | E | | 1/1980 | Rose et al. |
| 4,329,504 | A | | 5/1982 | Bugaut et al. |
| 4,736,756 | A | | 4/1988 | Grollier |
| 5,061,289 | A | | 10/1991 | Clausen et al. |
| 5,279,619 | A | | 1/1994 | Cotteret et al. |
| 5,380,340 | A | | 1/1995 | Neunhoeffer et al. |
| 5,534,267 | A | | 7/1996 | Neunhoeffer et al. |
| 5,645,610 | A | | 7/1997 | Balzer et al. |
| 5,663,366 | A | | 9/1997 | Neunhoeffer et al. |
| 5,756,079 | A | * | 5/1998 | Cauwet et al. ........... 424/70.19 |
| 5,766,576 | A | | 6/1998 | Löwe et al. |
| 5,935,587 | A | * | 8/1999 | Cauwet et al. .............. 424/401 |
| 6,045,779 | A | | 4/2000 | Mueller et al. |
| 6,284,003 | B1 | | 9/2001 | Rose et al. |
| 6,645,258 | B2 | | 11/2003 | Vidal et al. |
| 2002/0144700 | A1 | * | 10/2002 | Lim et al. .................... 132/208 |
| 2003/0037386 | A1 | | 2/2003 | Rose et al. |
| 2003/0150069 | A1 | | 8/2003 | Kleen et al. |
| 2004/0181883 | A1 | * | 9/2004 | Lagrand ........................ 8/405 |
| 2004/0187228 | A1 | * | 9/2004 | Lagrange ....................... 8/405 |
| 2004/0231071 | A1 | * | 11/2004 | Dreher .......................... 8/406 |

FOREIGN PATENT DOCUMENTS

| DE | 23 59 399 | 6/1975 |
| DE | 38 43 892 | 6/1990 |
| DE | 41 33 957 | 4/1993 |
| DE | 195 43 988 | 5/1997 |
| EP | 0 459 900 | 12/1991 |
| EP | 0 687 669 | 12/1995 |
| EP | 1 321 131 | 6/2003 |
| FR | 2 362 116 | 3/1978 |
| FR | 2 570 598 | 3/1986 |
| FR | 2 733 749 | 11/1996 |
| GB | 1 026 978 | 4/1966 |
| GB | 1 153 196 | 5/1969 |
| JP | 2-19576 | 1/1990 |
| JP | 5-163124 | 6/1993 |
| JP | 2526099 | 11/1996 |
| JP | 3053939 | 4/2000 |
| WO | WO 94/08969 | 4/1994 |
| WO | WO 94/08970 | 4/1994 |
| WO | WO 95/22312 | 8/1995 |
| WO | WO 96/15765 | 5/1996 |
| WO | WO 01/41714 | 6/2001 |
| WO | WO 01/97759 | 12/2001 |
| WO | WO 02/058656 | 8/2002 |
| WO | WO 02/058659 | 8/2002 |

OTHER PUBLICATIONS

French Search Report for FR 04/53186, dated Aug. 1, 2005.
English language Derwent Abstract of EP 1 321 131, Jun. 25, 2003.
English language Derwent Abstract of JP 2-19576 & 2526099, Jan. 23, 1990.
English language Derwent Abstract of JP 5-163124 & 3053939, Jun. 29, 1993.

* cited by examiner

*Primary Examiner*—Eisa B Elhilo
(74) *Attorney, Agent, or Firm*—Finnegan, Henderson, Farabow, Garrett & Dunner LLP

(57) ABSTRACT

Disclosed herein is a process for dyeing keratinous fibers comprising applying to the keratinous fibers at least one oxidation dyeing composition which comprises at least one oxidation base and at least one aromatic coupler substituted in the meta position by two amino groups, at least one of the amino group being primary, and washing the fibers, thus colored, with at least one detergent composition comprising at least one non-ionic surfactant chosen from alkylpolyglycoside surfactants and polyglycerolated surfactants.

31 Claims, No Drawings

PROCESS FOR WASHING COLORED KERATINOUS FIBERS WITH A COMPOSITION COMPRISING AT LEAST ONE NONIONIC SURFACTANT AND METHOD FOR PROTECTING THE COLOR

This application claims benefit of U.S. Provisional Application No. 60/645,068, filed Jan. 21, 2005, the contents of which are incorporated herein by reference. This application also claims benefit of priority under 35 U.S.C. § 119 to French Patent Application No. 04 53186, filed Dec. 23, 2004, the contents of which are also incorporated herein by reference.

Disclosed herein is a novel process for washing colored keratinous fibers, a dyeing kit comprising at least one oxidation dyeing composition and at least one detergent composition, and the use of these oxidation dyeing and detergent compositions for improving the resistance to shampoos of the coloring, for example, on sensitized hair.

It is known to dye keratinous fibers, including, human hair with dyeing compositions comprising oxidation dye precursors, generally known as oxidation bases, such as ortho- or para-phenylenediamines, ortho- or para-aminophenols and heterocyclic compounds. These oxidation bases are colorless or weakly colored compounds which, in combination with oxidizing substances, can give rise by an oxidative coupling process to colored compounds.

It is also known that the hues obtained with these oxidation bases can be varied by combining them with couplers or coloring modifiers, the latter being chosen, for example, from aromatic meta-diamines, meta-aminophenols, meta-diphenols and certain heterocyclic compounds, such as indole compounds.

The coloring obtained from this type of composition can be a permanent coloring. However, it has a tendency to become dull over time, for example, during shampooings.

Relatively nonaggressive shampoos have been developed in order to overcome this problem of the deterioration in the coloring during shampooings. For example, International Application Publication No. WO 2001/097759 discloses nonaggressive shampoos based on sugar-derived surfactants chosen from alkyl and alkenyl oligoglucosides or a fatty acid N-alkylpolyhydroxyalkylamide surfactant, these surfactants being combined with a fatty acid partial glyceride.

According to International Application Publication No. WO 2001/097759, this shampoo can make it possible to improve the resistance to washing operations of the colors and to increase the intensity of the coloring, whatever the type of dyeing employed.

Despite the development of this type of shampoo, the phenomenon of deterioration in the color during shampooings is still present, for example, on sensitized hair.

Accordingly, disclosed herein are novel techniques in order to overcome the problem related to the deterioration in the color, shampooing after shampooing, while retaining good usage qualities of the shampoo.

Thus, disclosed herein is a process for dyeing keratinous fibers comprising
   applying to the keratinous fibers at least one oxidation dyeing composition comprising, in an appropriate medium, at least one oxidation base and at least one aromatic coupler substituted in the meta position by two amino groups, at least one of the amino groups being primary, and
   washing said fibers with at least one detergent composition comprising at least one non-ionic surfactant chosen from alkylpolyglycoside surfactants and polyglycerolated surfactants.

According to the present disclosure, the at least one aromatic coupler can be chosen from heterocyclic or nonheterocyclic couplers.

As used herein, the term "primary amino group" is understood to mean an —NH$_2$ group.

The present disclosure also relates to a kit comprising:
   at least one oxidation dyeing composition comprising, in an appropriate medium, at least one oxidation base and at least one aromatic coupler substituted in the meta position by two amino groups, at least one of these amino groups being primary, and
   at least one detergent composition comprising at least one non-ionic surfactant chosen from alkylpolyglycoside surfactants and polyglycerolated surfactants.

The present disclosure still further relates to a method for protecting the coloring and/or for limiting the running of the coloring of keratinous fibers colored by an oxidation dyeing composition comprising at least one oxidation base and at least one coupler substituted in the meta position by two amino groups, at least one of the amino groups of which is primary; comprising:
   applying to the keratinous fibers at least one oxidation dyeing composition comprising, in an appropriate medium, at least one oxidation base and at least one aromatic coupler substituted in the meta position by two amino groups, at least one of these amino groups being primary, and
   washing said fibers with at least one detergent composition comprising at least one non-ionic surfactant chosen from alkylpolyglycoside surfactants and polyglycerolated surfactants.

The process and method as disclosed herein can make it possible to satisfactorily dye keratin fibers while limiting the deterioration in the color during repeated shampooings, to reduce the phenomenon of running of the color and to limit the staining of the skin and fabrics.

In one embodiment of the present disclosure, said keratinous fibers are sensitized hair. As used herein, the term "sensitized hair" is understood to mean hair which has, for example, been subjected to cosmetic treatments which chemically modify the individual hair, such as a permanent waving, a bleaching, hair straightening or a combination of these treatments, or, for example, the prolonged action of light or the mechanical action of repeated brushing.

According to one embodiment of the present disclosure, the at least one oxidation base can be chosen from para-phenylenediamines, double bases, para-aminophenols, ortho-aminophenols and heterocyclic oxidation bases.

Non-limiting mention may be made, among the para-phenylenediamines which can be used as oxidation base in the dyeing compositions in accordance with the present disclosure of the compounds of formula (I) and the addition salts thereof with an acid:

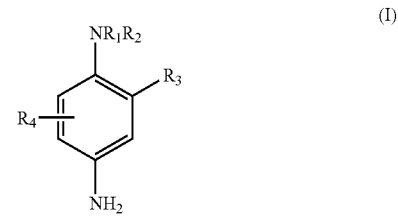

wherein:
R$_1$ is chosen from a hydrogen atom, C$_1$-C$_4$ alkyl radicals, C$_1$-C$_4$ monohydroxyalkyl radicals, C$_2$-C$_4$ polyhydroxyalkyl radicals, (C$_1$-C$_4$)alkoxy(C$_1$-C$_4$)alkyl radicals, and C$_1$-C$_4$ alkyl radicals substituted by a group chosen from nitrogenous, phenyl and/or 4'-aminophenyl groups;
R$_2$ is chosen from a hydrogen atom, C$_1$-C$_4$ alkyl radicals, C$_1$-C$_4$ monohydroxyalkyl radicals, C$_2$-C$_4$ polyhydroxyalkyl radicals, (C$_1$-C$_4$)alkoxy(C$_1$-C$_4$)alkyl radicals, and C$_1$-C$_4$ alkyl radicals substituted by a group chosen from nitrogenous groups;
R$_3$ is chosen from a hydrogen atom, a halogen atom, such as a chlorine, bromine, iodine or fluorine atoms, C$_1$-C$_4$ alkyl radicals, C$_1$-C$_4$ monohydroxyalkyl radicals, C$_1$-C$_4$ hydroxyalkoxy radicals, C$_1$-C$_4$ acetylaminoalkoxy radicals, C$_1$-C$_4$ mesylaminoalkoxy radicals and C$_1$-C$_4$ carbamoylaminoalkoxy radicals,
R$_4$ is chosen from a hydrogen atom, halogen atoms, and C$_1$-C$_4$ alkyl radicals.

Among the para-phenylenediamines of formula (I), non-limiting mention may further be made of, for example, para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl, β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, and the addition salts thereof with an acid.

The double bases which can be used as oxidation bases in the dyeing compositions in accordance with the present disclosure may, for example, be chosen from compounds of formula (II) and the addition salts thereof with an acid:

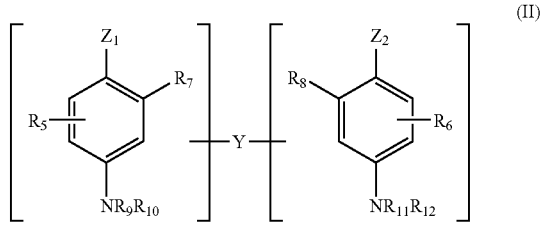

(II)

wherein:
Z$_1$ and Z$_2$, which may be identical or different, are independently chosen from hydroxyl and —NH$_2$ radicals which can be substituted by C$_1$-C$_4$ alkyl radicals or by a connecting arm Y;
the connecting arm Y is chosen from linear and branched alkylene chains comprising from 1 to 14 carbon atoms which can be interrupted or terminated by at least one nitrogenous groups and/or by at least one heteroatom, such as oxygen, sulphur or nitrogen atoms, and which is optionally substituted by at least one hydroxyl or C$_1$-C$_6$ alkoxy radical;
R$_5$ and R$_6$, which may be identical or different, are independently chosen from hydrogen atoms, halogen atoms, C$_1$-C$_4$ alkyl radicals, C$_1$-C$_4$ monohydroxyalkyl radicals, C$_2$-C$_4$ polyhydroxyalkyl radicals, C$_1$-C$_4$ aminoalkyl radicals and connecting arms Y;
R$_7$, R$_8$, R$_9$, R$_{10}$, R$_{11}$ and R$_{12}$, which may be identical or different, are independently chosen from hydrogen atoms, connecting arms Y and C$_1$-C$_4$ alkyl radicals; wherein the compounds of formula (II) comprise only a single connecting arm Y per molecule.

Non-limiting mention may be made, among the nitrogenous groups of the above formula (II), of amino, mono(C$_1$-C$_4$)alkylamino, di(C$_1$-C$_4$)alkylamino, tri(C$_1$-C$_4$)-alkylamino, monohydroxy(C$_1$-C$_4$)alkylamino, imidazolinium and ammonium radicals.

Non-limiting mention may be made, among the double bases of formula (II), of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino, 3'-methylphenyl)ethylenediamine, 1,8-bis(2,5-diaminophenoxy)-3,6-dioxaoctane, and the addition salts thereof with an acid.

Non-limiting mention may be made, among the para-aminophenols which can be used as oxidation bases in the dyeing compositions in accordance with the present disclosure, of the compounds corresponding to formula (III), and the addition salts thereof with an acid:

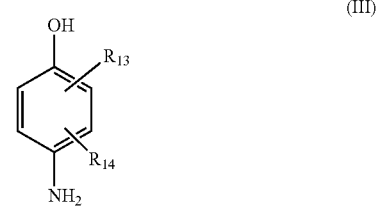

(III)

wherein:
R$_{13}$ is chosen from a hydrogen atom, halogen atoms, C$_1$-C$_4$ alkyl radicals, C$_1$-C$_4$ monohydroxyalkyl radicals, (C$_1$-C$_4$)alkoxy(C$_1$-C$_4$)alkyl radicals, C$_1$-C$_4$ aminoalkyl radicals and hydroxy(C$_1$-C$_4$)alkylamino(C$_1$-C$_4$)alkyl radicals;
R$_{14}$ is chosen from a hydrogen atom, halogen atoms, C$_1$-C$_4$ alkyl radicals, C$_1$-C$_4$ monohydroxyalkyl radicals, (C$_1$-C$_4$)alkoxy(C$_1$-C$_4$)alkyl radicals, C$_1$-C$_4$ aminoalkyl radicals, C$_1$-C$_4$ cyanoalkyl radicals and (C$_1$-C$_4$)alkoxy(C$_1$-C$_4$)alkyl radicals, wherein at least one of the R$_{13}$ or R$_{14}$ radicals is chosen from a hydrogen atom.

Mention may also be made, as para-aminophenols, of 4-amino-6-[(5'-amino-2'-hydroxy-3'-methylphenyl)methyl]-2-methylphenol and bis(5-amino-2-hydroxyphenyl)methane, and the addition salts thereof with an acid.

Mention may further be made, among the para-aminophenols of formula (III), of para-aminophenol, 4-amino-3-methylphenol, 4-amino-3-fluorophenol, 4-amino-3-(hydroxymethyl)phenol, 4-amino-2-methylphenol, 4-amino-2-(hydroxymethyl)phenol, 4-amino-2-(methoxymethyl)

phenol, 4-amino-2-(aminomethyl)phenol, 4-amino-2-[(β-hydroxyethyl)aminomethyl]phenol, 4-amino-2-fluorophenol, and the addition salts thereof with an acid.

Mention may also be made, among the ortho-aminophenols which can be used as oxidation bases in the dyeing compositions in accordance with the present disclosure of 2-aminophenol, 2-amino-5-methylphenol, 2-amino-6-methylphenol, 5-acetamido-2-aminophenol, and the addition salts thereof with an acid.

Mention may also be made, among the heterocyclic bases which can be used as oxidation bases in the dyeing compositions in accordance with the present disclosure, of the pyridine derivatives, the pyrimidine derivatives, the pyrazole derivatives, the pyrazolopyrimidine derivatives, and the addition salts thereof with an acid.

Non-limiting mention may be made, among the pyridine derivatives, of the compounds disclosed, for example, in British Patent Nos. GB 1 026 978 and GB 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine, and the addition salts thereof with an acid.

Non-limiting mention may be made, among the pyrimidine derivatives, of the compounds disclosed, for example, in German Patent No. DE 2 359 399 or Japanese Patent Nos. JP 88-169 571 and JP 91-333 495 or International Application Publication No. WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and the addition salts thereof with an acid.

Non-limiting mention may be made, among the pyrazole derivatives, of the diaminopyrazole compounds, such as 4,5-diaminopyrazoles or 3,4-diaminopyrazoles, for example those disclosed in German Patent Nos. DE 3 843 892 and DE 4 133 957 and International Application Publication Nos. WO 94/08969 and WO 94/08970, French Patent Application No. FR-A-2 733 749 and German Application No. DE 195 43 988, such as 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-(hydroxymethyl)pyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-(methylamino) pyrazole, 3,5-diamino-4-(β-hydroxyethyl)amino-1-methylpyrazole, and the addition salts thereof with an acid.

Among the pyrazolopyrimidine derivatives that may be used, non-limiting mention may be made of the pyrazolo[1,5-a]pyrimidines of formula (IV), the addition salts thereof with an acid or with a base, and their tautomeric forms, when a tautomeric equilibrium exists:

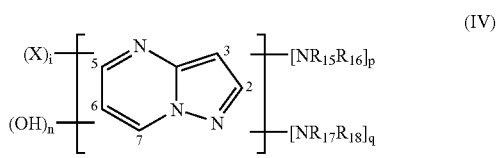

wherein:

$R_{15}$, $R_{16}$, $R_{17}$ and $R_{18}$, which may be identical or different, are independently chosen from hydrogen atoms, $C_1$-$C_4$ alkyl radicals, aryl radicals, $C_1$-$C_4$ hydroxyalkyl radicals, $C_2$-$C_4$ polyhydroxyalkyl radicals, ($C_1$-$C_4$)alkoxy($C_1$-$C_4$)alkyl radicals, $C_1$-$C_4$ aminoalkyl radicals wherein the amine is optionally protected by an acetyl, ureido or sulphonyl radicals, ($C_1$-$C_4$)alkylamino($C_1$-$C_4$)alkyl radicals, di[($C_1$-$C_4$) alkyl]amino($C_1$-$C_4$)alkyl radicals wherein the dialkyl radicals may optionally form a carbon ring or a heterocycle with 5 or 6 ring members, hydroxy($C_1$-$C_4$)alkylamino($C_1$-$C_4$)alkyl radicals and di[hydroxy($C_1$-$C_4$)alkyl]amino($C_1$-$C_4$)alkyl radicals;

X, which may be identical or different, are independently chosen from a hydrogen atom, $C_1$-$C_4$ alkyl radicals, aryl radicals, $C_1$-$C_4$ hydroxyalkyl radicals, $C_2$-$C_4$ polyhydroxyalkyl radicals, amino($C_1$-$C_4$)alkyl radicals, ($C_1$-$C_4$) alkylamino($C_1$-$C_4$)alkyl radicals, di[($C_1$-$C_4$)]alkyl]amino ($C_1$-$C_4$)alkyl radicals wherein the dialkyls optionally form a carbon ring or a heterocycle with 5 or 6 ring members, hydroxy($C_1$-$C_4$)alkylamino($C_1$-C4)alkyl radicals, di[hydroxy($C_1$-$C_4$)alkyl]amino($C_1$-$C_4$)alkyl radicals, amino radicals, ($C_1$-$C_4$)alkylamino radicals, di[($C_1$-$C_4$)alkyl] amino radicals, halogens atom, a carboxylic acid group or a sulphonic acid group;

i is a number chosen from 0, 1, 2 or 3;

p is a number chosen from 0 or 1;

q is a number chosen from 0 or 1;

n is a number chosen from 0 or 1;

with the proviso that the sum p+q is other than 0; and when p+q is equal to 2, then n is 0 and the $NR_{15}R_{16}$ and $NR_{17}R_{18}$ groups occupy the (2,3); (5,6); (6,7); (3,5) or (3,7) positions;

when p+q is equal to 1, then n is 1 and the $NR_{15}R_{16}$ (or $NR_{17}R_{18}$) group and the OH group occupy the (2,3); (5,6); (6,7); (3,5) or (3,7) positions.

Non-limiting mention may be made, among the pyrazolo (1,5-a]pyrimidines of formula (IV), of pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol; 2-(7-aminopyrazolo[1,5-a]pyrimidin-3-ylamino)ethanol; 2-[(3-aminopyrazolo[1,5-a]pyrimidin-7-yl)(2-hydroxyethyl)amino]ethanol; 2-[(7-aminopyrazolo[1,5-a]pyrimidin-3-yl)(2-hydroxyethyl)amino]ethanol; 5,6-dimethylpyrazolo[1,5-a]pyrimidine-3,7-diamine; 2,6-dimethylpyrazolo[1,5-a]pyrimidine-3,7-diamine; 2,5,N7,N7-tetramethylpyrazolo[1,5-a]pyrimidine-3,7-diamine; and the addition salts thereof and their tautomeric forms, when a tautomeric equilibrium exists.

The at least one oxidation base present in the composition disclosed herein may be present in an amount ranging from 0.001 to 10% by weight, relative to the total weight of the dyeing composition, for example, from 0.005 to 6%.

According to another embodiment of the present disclosure, the at least one coupler may be substituted solely by the two amino groups in the meta position. They may also be substituted by at least one additional substituents, for example, one or two additional groups, on the aromatic ring.

The aromatic ring can be, for example, a benzene, naphthalene, pyridine or pyrimidine ring.

According to another embodiment of the present disclosure the aromatic coupler substituted in the meta position by two amino groups can be a meta-phenylenediamine coupler, at least one of the amino groups of which is primary.

Mention may be made, for example, of heterocyclic aromatic couplers chosen from 2,6-dimethoxypyridine-3,5-diamine and pyridine-2,6-diamine, or their addition salts.

Non-limiting mention may be made, for example, of benzene couplers chosen from meta-phenylenediamine, 2,4-diaminophenoxyethanol, 1-methoxy-2-amino-4-(2'-hydroxyethylamino)benzene, 4-fluoro-6-methylbenzene-1,3-diamine, 1-amino-3-(N,N-bis(β-hydroxyethyl)amino)benzene, 1,3-bis(2,4-diaminophenoxy)propane, 1-(β-aminoethyloxy)-2,4-diaminobenzene, 1-(β-hydroxyethyl)-2,4-diaminobenzene, (2,4-diaminophenoxy)acetic acid, 4,6-bis(β-hydroxyethoxy)-1,3-diaminobenzene, 2,4-diamino-5-methylethoxybenzene, 2,4-diamino-5-(β-hydroxyethyloxy) toluene, 2,4-dimethoxy-1,3-diaminobenzene, and the addition salts thereof.

According to another embodiment of the present disclosure, the meta-phenylenediamine coupler may be chosen from a meta-phenylenediamine coupler, the two amino groups of which are primary. Mention may be made, for example, of meta-phenylenediamine, 2,4-diaminophenoxyethanol, 4-fluoro-6-methylbenzene-1,3-diamine, 1,3-bis(2,4-diaminophenoxy)propane, 1-(β-aminoethyloxy)-2,4-diaminobenzene, 1-(β-hydroxyethyl)-2,4-diaminobenzene, (2,4-diaminophenoxy)acetic acid, 4,6-bis(β-hydroxyethoxy)-1,3-diaminobenzene, 2,4-diamino-5-methylethoxybenzene, 2,4-diamino-5-(β-hydroxyethyloxy)toluene, 2,4-dimethoxy-1,3-diaminobenzene, and the addition salts thereof.

The oxidation dyeing composition may additionally comprise at least one coupler conventionally used for the dyeing of keratinous fibers. Non-limiting mention may be made, among these couplers, of meta-phenylenediamines other than the meta-phenylenediamines defined above, meta-aminophenols, meta-diphenols, naphthalene couplers, heterocyclic couplers, and the addition salts thereof.

Mention may be made, by way of non-limiting example, of 2-methyl-5-aminophenol, 5-(N-(β-hydroxyethyl)amino)-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 1,3-bis(2,4-diaminophenoxy)propane, 3-ureidoaniline, sesamol, 1-(β-hydroxyethylamino)-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 1-(N-(β-hydroxyethyl)amino)-3,4-methylenedioxybenzene, 2,6-bis(β-hydroxyethylamino)toluene, and the addition salts thereof with an acid.

The at least one coupler may be present in the composition of the present disclosure in an amount ranging from 0.001 to 10% by weight, relative to the total weight of the dyeing composition, for example, from 0.005 to 6%.

Generally, the addition salts with an acid that can be used in the context of the dyeing compositions disclosed herein (oxidation bases and couplers) are chosen, for example, from hydrochlorides, hydrobromides, sulphates, tartrates, lactates and acetates.

In one embodiment, the dyeing composition disclosed herein may additionally comprise at least one direct dye which may be chosen from nitrobenzene dyes, azo direct dyes and methine direct dyes. These direct dyes may be nonionic, anionic or cationic in nature.

The medium appropriate for the dyeing, also referred to as dyeing vehicle, is generally composed of water, or of a mixture of water and of at least one organic solvent, in order to dissolve the compounds which would be insufficiently soluble in water. Non-limiting mention may be made, among the organic solvents that may be used, for example, of lower $C_1$-$C_4$ alkanols, such as ethanol and isopropanol; polyols and polyol ethers, such as 2-butoxyethanol, propylene glycol, propylene glycol monomethyl ether, diethylene glycol monoethyl ether and diethylene glycol monomethyl ether, and also aromatic alcohols, such as benzyl alcohol or phenoxyethanol, and their mixtures.

The at least one solvent may be present in an amount ranging from 1 to 40% by weight, relative to the total weight of the dyeing composition, for example, ranging from 5 to 30%.

The dyeing composition disclosed herein may also include at least one adjuvant conventionally used in compositions for dyeing the hair, such as anionic, cationic, nonionic, amphoteric and zwitterionic surface-active agents; anionic, cationic, nonionic, amphoteric and zwitterionic polymers; inorganic and organic thickening agents, for example, anionic, cationic, nonionic and amphoteric polymeric associative thickeners; antioxidants; penetrating agents; sequestering agents; fragrances; buffers; dispersants; conditioning agents, such as, for example, volatile and nonvolatile, and modified unmodified silicones; film-forming agents; ceramides; preservatives; and opacifiers.

The at least one adjuvant may be present in an amount ranging from, for each adjuvant, 0.01 to 20% by weight, relative to the total weight of the composition.

A person skilled in the art will take care to choose this or these optional additional compounds so that the beneficial properties intrinsically associated with the compositions and processes in accordance with the present disclosure are not, or not substantially, detrimentally affected by the envisaged addition or additions.

The pH of the dyeing composition of the present disclosure may range from 3 to 12, for example, from 5 to 11. It can be adjusted to the desired value using acidifying or basifying agents generally used in dyeing keratinous fibers or else using conventional buffer systems.

Mention may be made, among acidifying agents, by way of non-limiting example, of inorganic or organic acids such as hydrochloric acid; orthophosphoric acid; sulphuric acid; carboxylic acids such as acetic acid, tartaric acid, citric acid or lactic acid; or sulphonic acids.

Mention may be made, among the basifying agents that may be used, by way of non-limiting example, of ammonia; alkaline carbonates; alkanolamines, such as mono-, di- and triethanolamines, and the derivatives thereof; sodium hydroxide; potassium hydroxide, and the compounds of following formula (II):

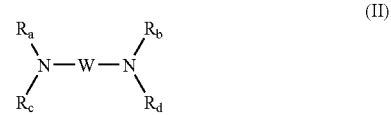

wherein

W is chosen from propylene residues optionally substituted by hydroxyl groups or $C_1$-$C_4$ alkyl radicals and $R_a$, $R_b$, $R_c$ and $R_d$, which may be identical or different, are independently chosen from hydrogen atoms, and $C_1$-$C_4$ alkyl and $C_1$-$C_4$ hydroxyalkyl radicals.

The dyeing composition used in the process disclosed herein can be provided in various forms, such as in the form of liquids, creams or gels or in any other form appropriate for carrying out the dyeing of keratinous fibers, including, human hair.

The oxidation dyeing stage may be carried out in the presence of at least one oxidizing agent. The at least one oxidizing agent, applied to the keratinous fibers in the presence of the dyeing composition for a period of sufficient time, can make it possible to develop the desired coloring. The color can be revealed at acidic, neutral or alkaline pH and the at least one oxidizing agent may be added to the composition disclosed herein at the moment of use, or it can be employed starting from an oxidizing composition comprising it, applied simultaneously or sequentially with the composition of the present disclosure.

According to one embodiment, the composition according to the present disclosure is mixed, for example, at the moment of use, with a composition comprising, in a medium appropriate for the dyeing, at least one oxidizing agent, this at least one oxidizing agent being present in an amount sufficient to develop a coloring. The mixture obtained is subsequently applied to keratinous fibers. After a period of leave-in time ranging from 3 to 50 minutes, for example 5 to 30 minutes, the keratinous fibers are rinsed, washed with a shampoo, rinsed again and then dried.

The oxidizing agents conventionally used for the oxidation dyeing of keratinous fibers that may be used, include, for example, hydrogen peroxide, urea peroxide, alkali metal bromates, persalts such as perborates and persulphates, peracids and oxidase enzymes, among which non-limiting mentioned may be made of peroxidases, 2-electron oxidoreductases such as uricases, and 4-electron oxygenases, such as laccases. Hydrogen peroxide is used, for example, in one embodiment.

The oxidizing composition may also include at least one adjuvant chosen from the various adjuvants conventionally used in compositions for dyeing the hair and as defined above.

The pH of the oxidizing composition including the at least one oxidizing agent is such that, after mixing with the dyeing composition, the pH of the resulting composition applied to the keratinous fibers ranges from 3 to 12, for example, from 5 to 11. It can be adjusted to the desired value using acidifying or basifying agents commonly used in dyeing keratinous fibers and as defined above.

The oxidation dyeing composition which is finally applied to the keratinous fibers can be provided in various forms, such as in the form of liquids, creams or gels or in any other form appropriate for dyeing keratinous fibers, including, human hair.

The washing stage of the process disclosed herein is carried out with a detergent composition which comprises at least one nonionic surfactant chosen from alkylpolyglycoside surfactants and polyglycerolated surfactants.

The alkylpolyglucoside surfactants are well known in the art and can be chosen from, for example, those of formula (V):

$$R_1O-(R_2O)_t(G)_v \qquad (V)$$

wherein:

$R_1$ is chosen from linear and branched alkyl and alkenyl radicals comprising from 8 to 24 carbon atoms, and alkylphenyl radicals, the linear or branched alkyl radicals of which comprise from 8 to 24 carbon atoms, $R_2$ is chosen from alkylene radicals comprising from 2 to 4 carbon atoms, G is chosen from a reduced sugar comprising from 5 to 6 carbon atoms, t is a number ranging from 0 to 10, and v is a number ranging from 1 to 15.

In one embodiment, according to the present disclosure, $R_1$ may be chosen from saturated and unsaturated, linear and branched alkyl radicals comprising from 8 to 18 carbon atoms, t is a number ranging from 0 to 3, or, for example, 0, and G is chosen from glucose, fructose and galactose, for instance, glucose. The degree of polymerization, i.e., the value of v in the formula (II), may range from 1 to 15, for example, from 1 to 4. The mean degree of polymerization, for example, can range from 1 to 2.

The glycoside bonds between the sugar units are of 1-6 or 1-4 type, for example, of 1-4 type.

Compounds of formula (V) can be chosen from, for example, the products sold by Cognis under the names PLANTAREN® (600 CS/U, 1200 and 2000) or PLANTACARE® (818, 1200 and 2000); the products sold by Seppic under the names TRITON CG 110 (or ORAMIX CG 110) and TRITON CG 312 (or ORAMIX NS 10); the products sold by BASF under the name LUTENSOL GB 70 or those sold by Chem Y under the name AG10 LK.

Non-limiting mention may also be made, for example, of the $C_8/C_{16}$ alkyl 1,4-polyglucoside in 53% aqueous solution sold by Cognis under the name PLANTACARE® 818 UP.

The polyglycerolated surfactant can be chosen from the compounds of formulae:

$RO[CH_2CH(CH_2OH)O]_mH$, $RO[CH(CH_2OH)CH_2O]_mH$, and $RO[CH_2CH(OH)CH_2O]_mH$, wherein:

R is chosen from saturated and unsaturated, linear and branched, optionally mono- or polyhydroxylated, hydrocarbon radicals comprising from 8 to 40 carbon atoms, for example from 10 to 30, and m is a number ranging from 1 to 10, for example from 1.5 to 6.

R may also comprise at least one heteroatom, such as, for example, oxygen and nitrogen. For instance, R can optionally comprise at least one hydroxyl and/or ether and/or amide groups.

R may, for example, be chosen from $C_{10}$-$C_{20}$ alkyl and alkenyl radicals which are optionally mono- or polyhydroxylated.

Use may be made, for example, of the polyglycerolated (3.5 mol) hydroxylauryl ether sold under the name CHIMEXANE® NF by Chimex.

In accordance with another embodiment of the present disclosure, the at least one nonionic surfactant can be present in a total amount ranging from 4 to 50% by weight, relative to the total weight of the detergent composition, for example, from 6 to 30%.

The detergent composition may comprise at least one other surfactant conventionally used in detergent compositions, for example at least one nonionic surfactant other than those cited above, at least one amphoteric or zwitterionic surfactant or at least one anionic surfactant, for example mild anionic surfactants.

For example, mention may be made, among the nonionic surfactants other than those of previously disclosed herein, of:

oxyalkylenated fatty alcohols;
oxyalkylenated alkylphenols, wherein the alkyl chain is chosen from $C_8$-$C_{18}$ alkyls;
oxyalkylenated or polyglycerolated fatty amides;
oxyalkylenated fatty amines;
oxyalkylenated vegetable oils;
sorbitan esters of fatty acids which are optionally oxyalkylenated;
sucrose esters of fatty acids which are optionally oxyalkylenated;
polyethylene glycol esters of fatty acids;
N-alkylglucamine derivatives;
amine oxides, such as oxides of ($C_{10}$-$C_{14}$)alkylamines or oxides of N-acylaminopropylmorpholine;
copolymers of ethylene oxide and of propylene oxide.

As used herein, the term "fatty chain" is understood to mean a saturated or unsaturated and linear or branched hydrocarbon chain comprising from 6 to 30 carbon atoms, for example, from 8 to 24 carbon atoms.

For example, the mean number of oxyalkylene units may range from 2 to 30. For instance, they may be oxyethylene or oxypropylene units or mixtures thereof.

Non-limiting mention may be made, among amphoteric or zwitterionic surfactants that may be used, of secondary or tertiary aliphatic amine derivatives wherein the aliphatic radicals is a linear or branched chain comprising from 8 to 18 carbon atoms and comprising at least one water-solubilizing anionic group (for example, carboxylate, sulphonate, sulphate, phosphate or phosphonate); non-limiting mention may also be made of ($C_8$-$C_{20}$)alkyl betaines, sulphobetaines, ($C_8$-$C_{20}$)alkyl amido($C_1$-$C_6$)alkyl betaines or ($C_8$-$C_{20}$)alkyl amido($C_1$-$C_6$)alkyl sulphobetaines.

Non-limiting mention may be made, among the amine derivatives, of the products sold under the Miranol name, such as disclosed in U.S. Pat. Nos. 2,528,378 and 2,781,354 and categorized in the CTFA dictionary, 5th edition, 1993, under the names Disodium Cocoamphodiacetate, Disodium Lauroamphodiacetate, Disodium Caprylamphodiacetate, Disodium Capryloamphodiacetate, Disodium Cocoamphodipropionate, Disodium Lauroamphodipropionate, Disodium Caprylamphodipropionate, Disodium Capryloamphodipropionate, Lauroamphodipropionic Acid, Cocoamphodipropionic Acid, Disodium Cocoamphocarboxy Ethyl Hydroxypropyl Sulfonate.

Non-limiting mention may be made, for example, of the cocoamphodiacetate sold under the trade name MIRANOL® C2M concentrate by RhodiaChimie.

Among the mild anionic surfactants, mention may be made, for instance, of compounds with the following formulae, and mixtures thereof:

polyoxyalkylenated alkyl ether carboxylic acids,
polyoxyalkylenated alkylaryl ether carboxylic acids,
polyoxyalkylenated alkylamido ether carboxylic acids, for example, those comprising 2 to 50 ethylene groups,
alkyl D-galactosideuronic acids,
acyl sarcosinates or acyl glutamates;
alkylpolyglycosidecarboxylic esters;
salts of fatty acids.

Use may, for example, be made of polyoxyalkylenated alkyl ether carboxylic acids, such as, for example, lauryl ether carboxylic acid (4.5 EO), for example sold under the name AKYPO RLM 45 CA from Kao.

The at least one amphoteric, zwitterionic and/or mild anionic surfactants, when present, may be present in an amount ranging from 4 to 50% by weight, with respect to the total weight of the detergent composition.

The composition may, for example, also comprise small amounts of alkyl ether sulphates or of alkyl sulphates. These amounts may be, for example, less than 5%.

The detergent composition can additionally comprise at least one additive chosen from those which are conventional in the field, such as, by way of non-limiting example: reducing agents, oxidizing agents, sequestering agents, softening agents, antifoaming agents, moisturizing agents, emollients, basifying agents, plasticizers, sunscreens, pigments, inorganic fillers, clays, colloidal minerals, pearlescent agents, fragrances, peptizing agents, preservatives, fixing or nonfixing polymers, proteins, vitamins, antidandruff agents, aliphatic or aromatic alcohols, for example, ethanol or benzyl alcohol, modified or unmodified polyols, such as glycerol, glycol, propylene glycol, dipropylene glycol, butylene glycol or butyl diglycol, volatile silicones, mineral, organic or vegetable oils, oxyethylenated or nonoxyethylenated waxes, paraffins, fatty acids, associative or nonassociative thickening polymers, fatty amides, fatty esters, fatty alcohols or conditioning agents, for example, cationic conditioning agents, such as cationic polymers comprising units comprising primary, secondary, tertiary and/or quaternary amine groups which can either form part of the main polymer chain or be carried by a side substituent directly connected to the main polymer chain.

The at least one adjuvant mentioned above may, for example, be present in an amount, for each adjuvant, ranging from 0.01 to 20% by weight, relative to the total weight of the composition.

The detergent compositions can be provided in various formulation forms, such as a lotion, a spray, an aerosol foam, a foam pump, and the like.

The process disclosed herein can comprise other stages. For example, it can comprise stages of rinsing the keratinous fibers, stages of conditioning the keratinous fibers, or drying stages. According to one embodiment, the process comprises at least one intermediate washing stage comprising applying to the keratinous fibers a detergent composition comprising a conventional anionic surfactant, for example, chosen from alkyl ether sulphates and alkyl sulphates.

Furthermore, the implementation of the stages of dyeing and of washing the keratinous fibers with the compositions of the present disclosure can be delayed in time, for example with a gap of at least 12 hours between the dyeing stage and the stage or stages of washing with the detergent composition of the present disclosure. It is also possible to carry out several washing stages using the detergent composition of the present disclosure for one single dyeing stage.

Another embodiment of the present disclosure is a kit comprising at least one oxidation dyeing composition comprising, in an appropriate medium, at least one oxidation base and at least one aromatic coupler substituted in the meta position by two amino groups, at least one of these amino groups being primary, and at least one detergent composition comprising at least one non-ionic surfactant chosen from alkylpolyglycoside surfactants and polyglycerolated surfactants.

According to another embodiment, the kit further comprises a composition comprising at least one oxidizing agent.

Still yet another embodiment of the present disclosure is a process for protecting the coloring and/or for limiting the running of the coloring of dyed keratinous fibers that were dyed from an oxidation dyeing composition comprising at least one oxidation base and at least one coupler substituted in the meta position by two amino groups, at least one of the amino groups of which is primary; comprising:

applying to the keratinous fibers at least one oxidation dyeing composition comprising, in an appropriate medium, at least one oxidation base and at least one aromatic coupler substituted in the meta position by two amino groups, at least one of these amino groups being primary, and washing said fibers with at least one detergent composition comprising at least one non-ionic surfactant chosen from alkylpolyglycoside surfactants and polyglycerolated surfactants.

According to another embodiment, the colored keratinous fibers are sensitized keratinous fibers.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the embodiments disclosed herein. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosed embodiments are approximations, unless otherwise indicated the numerical values set forth in the specific examples are reported as precisely as possible. Any numerical value, however, inherently contain certain errors necessarily resulting from the standard deviation found in their respective testing measurements.

The embodiments disclosed herein are illustrated in greater detail, in a non-limiting manner, by the examples described below.

EXAMPLES

Example 1

The following dyeing compositions were prepared from the various meta-phenylenediamine couplers described below:

2,4-diamino-phenoxyethanol·2HCl 1-methoxy-2-amino-4-(2'-hydroxyethylamino)benzene·2HCl 2,6-bis(2-hydroxyethylamino)-1-methylbenzene

| | Composition 1 (Present Disclosure) | Composition 2 (Present Disclosure) | Composition 3 (Comparative) |
|---|---|---|---|
| Decyl glucoside as a 60% aqueous solution of ORAMIX ® CG 110 (Seppic) | 5.4 g | 5.4 g | 5.4 g |
| 96° Denatured ethyl alcohol | 18 g | 18 g | 18 g |
| Benzyl alcohol | 1.8 g | 1.8 g | 1.8 g |
| Polyethylene glycol (8 EO) | 2.7 g | 2.7 g | 2.7 g |
| 40% Pentasodium pentetate in water | 1.08 g | 1.08 g | 1.08 g |
| Sodium metabisulphite | 0.205 g | 0.205 g | 0.205 g |
| 2,4-Diaminophenoxy-ethanol·HCl | 6 × 10$^{-3}$ mol | — | — |
| 1-Methoxy-2-amino-4-(2'-hydroxyethylamino)benzene·2HCl | — | 6 × 10$^{-3}$ mol | — |
| 2,6-Bis(2-hydroxyethylamino)-1-methylbenzene | — | — | 6 × 10$^{-3}$ mol |
| para-Phenylenediamine | 6 × 10$^{-3}$ mol | 6 × 10$^{-3}$ mol | 6 × 10$^{-3}$ mol |
| 20.5% Ammonia | 10 g | 10 g | 10 g |
| Demineralized water | q.s. for 100 | q.s. for 100 | q.s. for 100 |

At the time of use, each of the above compositions was mixed, weight for weight, with aqueous hydrogen peroxide solution (aqueous hydrogen peroxide solution, L'Oreal Professional 20 volume (6%)).

The mixture was subsequently applied to locks of natural hair comprising 90% of white hairs, highly bleached and permed, in a proportion of 10 g of dye mixture/g of lock. The period of leave-in time was 15 minutes on each side of the lock.

The hair was subsequently rinsed with water and then washed with a commercial shampoo (DOP camomile shampoo). The locks were subsequently dried under a hair drier at 60° C. for 30 minutes.

Washing Stages:

48 hours after carrying out the dyeing operations described above, the locks were subjected to washing tests with a detergent composition comprising a nonionic surfactant as described in Table 3:

TABLE 3

|  | Detergent Composition 1 |
|---|---|
| 53% Coco glucoside in water (PLANTACARE ® 818 UP, Cognis) | 28.30 g |
| Citric acid | q.s. for pH = 6 |
| Water | q.s. for 100 |

Three shampooings were carried out, the locks being dried under a hair drier (30 minutes at 60° C.) between each shampooing.

Before the washing and after the three washing stages, the coloring of the locks was evaluated visually, and by measuring the (L*, a*, b*) values using the Minolta CM 2022 spectrocolorimeter.

The deterioration in the coloring before and after the three stages of washing using detergent composition 1 is expressed in ΔE according to the following formula:

$$\Delta E_{i(after\ washing-before\ washing)} = \sqrt{(\Delta L_i^{*2} + \Delta a_i^{*2} + \Delta b_i^{*2})}$$

Results:

TABLE 4

| Colouring | Composition 1 (present disclosure) | Composition 2 (present disclosure) | Composition 3 (Comparative) |
|---|---|---|---|
| Deterioration in color (ΔE) | 4.7 | 9 | 31 |

These results show a very marked improvement in the resistance of the coloring when detergent composition 1 was applied to locks dyed with meta-phenylenediamine oxidation couplers substituted in the meta position by two amino groups, at least one of the amino groups of which is primary.

It is also found that the running of the color in the water and in the foam was less significant when using the processes of the present disclosure.

What is claimed is:

1. A process for dyeing keratinous fibers comprising:
   applying to the keratinous fibers at least one oxidation dyeing composition comprising, in an appropriate medium, at least one oxidation base and at least one aromatic coupler substituted in the meta position by two amino groups, at least one of the amino groups being primary, and
   washing said fibers with at least one detergent composition comprising at least one non-ionic surfactant chosen from alkylpolyglycoside surfactants and polyglycerolated surfactants.

2. The process according to claim 1, wherein the at least one oxidation base is chosen from para-phenylenediamines, double bases, para-aminophenols, ortho-aminophenols and heterocyclic oxidation bases.

3. The process according to claim 1, wherein the at least one oxidation base is present in an amount ranging from 0.001% to 10% by weight, relative to the total weight of the dyeing composition.

4. The process according to claim 1, wherein the at least one aromatic coupler substituted in the meta position by two amino groups is chosen from meta-phenylenediamine couplers.

5. The process according to claim 4, wherein the at least one meta-phenylenediamine coupler is chosen from those that have two amino groups which are primary amino groups.

6. The process according to claim 4, wherein the at least one meta-phenylenediamine coupler is chosen from meta-phenylenediamine, 2,4-diaminophenoxyethanol, 1-methoxy-2-amino-4-(2'-hydroxyethylamino)benzene, 4-fluoro-6-methylbenzene-1,3-diamine, 1-amino-3-(N,N-bis(β-hydroxyethyl)amino)benzene, 1,3-bis(2,4-diaminophenoxy)propane, 1-(β-aminoethyloxy)-2,4-diaminobenzene, 1-(β-hydroxyethyl)-2,4-diaminobenzene, (2,4-diaminophenoxy)acetic acid, 4,6-bis(β-hydroxyethoxy)-1,3-diaminobenzene, 2,4-diamino-5-methylethoxybenzene, 2,4-diamino-5-(β-hydroxyethyloxy)toluene, 2,4-dimethoxy-1,3-diaminobenzene and the addition salts thereof.

7. The process according to claim 1, wherein the at least one aromatic coupler is present in an amount, for each coupler, ranging from 0.001% to 10% by weight, relative to the total weight of the dyeing composition.

8. The process according to claim 1, wherein the at least one oxidation dyeing composition comprises at least one oxidizing agent.

9. The process according to claim 8, wherein the at least one oxidizing agent is chosen from hydrogen peroxide, urea peroxide, alkali metal bromates, alkali metal ferricyanides, persalts and oxidoreduction enzymes.

10. The process according to claim 1, wherein the at least one oxidation dyeing composition comprises at least one direct dye.

11. The process according to claim 1, wherein the at least one alkylpolyglycoside surfactant is chosen from compounds of formula (V):

$$R_1O-(R_2O)_t(G)_v \tag{V}$$

wherein:
   $R_1$ is chosen from linear and branched alkyls and alkenyl radicals comprising from 8 to 24 carbon atoms, and alkylphenyl radicals, the linear or branched alkyl radicals of which comprise from 8 to 24 carbon atoms,
   $R_2$ is chosen from alkylene radicals comprising from 2 to 4 carbon atoms,
   G is chosen from a reduced sugar comprising from 5 to 6 carbon atoms,
   t is a number ranging from 0 to 10, and
   v is a number ranging from 1 to 15.

12. The process according to claim 1, wherein the at least one polyglycerolated surfactant is chosen from the compounds of formulae:

$$RO[CH_2CH(CH_2OH)O]_mH,$$

$$RO[CH(CH_2OH)CH_2O]_mH, \text{ and}$$

$$RO[CH_2CH(OH)CH_2O]_mH,$$

wherein:
R is chosen from saturated and unsaturated, linear and branched, optionally mono- and/or polyhydroxylated, hydrocarbon radicals comprising from 8 to 40 carbon atoms and
m is a number ranging from 1 to 10.

13. The process according to claim 12, wherein R is chosen from saturated and unsaturated, linear and branched, optionally mono- and/or polyhydroxylated, hydrocarbon radicals comprising from 10 to 30 carbon atoms.

14. The process according to claim 12, wherein m is a number ranging from 1.6 to 6.

15. The process according to claim 1, wherein the at least one non-ionic surfactant is present in a total amount ranging from 4% to 50% by weight, relative to the total weight of the detergent composition.

16. The process according to claim 1, wherein the at least one detergent composition additionally comprises at least one surfactant chosen from nonionic surfactants other than alkylpolyglycoside surfactants and polyglycerolated surfactants, amphoteric surfactants, zwitterionic surfactants and mild anionic surfactants.

17. The process according to claim 15, wherein the at least one detergent composition comprises at least one additional surfactant chosen from:
oxyalkylenated fatty alcohols;
oxyalkylenated alkylphenols, wherein the alkyl chain is chosen from $C_8$-$C_{18}$ alkyls;
oxyalkylenated and polyglycerolated fatty amides;
oxyalkylenated fatty amines;
oxyalkylenated vegetable oils;
sorbitan esters of fatty acids which are optionally oxyalkylenated;
sucrose esters of fatty acids which are optionally oxyalkylenated;
polyethylene glycol esters of fatty acids;
N-alkylglucamine derivatives;
amine oxides; and
copolymers of ethylene oxide and of propylene oxide.

18. The process according to claim 17, wherein the amine oxides are chosen from oxides of $(C_{10}$-$C_{14})$alkylamines and oxides of N-acylaminopropylmorpholine.

19. The process according to claim 1, wherein the at least one detergent composition comprises at least one conditioning agent.

20. The process according to claim 19, wherein the at least one conditioning agent is chosen from cationic conditioning agents.

21. The process according to claim 1, wherein the detergent composition comprises at least one surfactant chosen from alkyl sulphate surfactants and alkyl ether sulphate surfactants.

22. The process according to claim 21, wherein the at least one surfactant chosen from alkyl ether sulphate and/or alkyl sulphate surfactants is present in an amount of less than 5% by weight, relative to the total weight of the detergent composition.

23. The process according to claim 1, comprising washing said keratinous fibers with a detergent composition comprising at least one anionic surfactant chosen from alkyl ether sulphates and alkyl sulphates, before washing said keratinous fibers with at least one detergent composition comprising at least one non-ionic surfactant chosen from alkylpolyglycoside surfactants and polyglycerolated surfactants.

24. The process according to claim 1, comprising at least one additional stage chosen from rinsing, washing, conditioning and drying.

25. The process according to claim 1, wherein there is a gap in time of at least 12 hours after the application of the dyeing composition to said keratinous fibers before washing said keratinous fibers with at least one detergent composition comprising at least one non-ionic surfactant chosen from alkylpolyglycoside surfactants and polyglycerolated surfactants.

26. The process according to claim 1, wherein said keratinous fibers are washed several times with the at least one detergent composition comprising at least one non-ionic surfactant chosen from alkylpolyglycoside surfactants and polyglycerolated surfactants.

27. The process according to claim 1, wherein said keratinous fibers are sensitized keratinous fibers.

28. A kit comprising:
at least one oxidation dyeing composition comprising, in an appropriate medium, at least one oxidation base and at least one aromatic coupler substituted in the meta position by two amino groups, at least one of the amino groups being primary, and
at least one detergent composition comprising at least one non-ionic surfactant chosen from alkylpolyglycoside surfactants and polyglycerolated surfactants.

29. A kit according to claim 28, comprising a composition comprising at least one oxidizing agent.

30. A method for protecting the coloring of and/or for limiting the running of the coloring of keratinous fibers dyed with an oxidation dyeing composition comprising at least one oxidation base and at least one aromatic coupler substituted in the meta position by two amino groups, at least one of the amino groups of which is primary; comprising:
applying to the keratinous fibers at least one oxidation dyeing composition comprising, in an appropriate medium, at least one oxidation base and at least one aromatic coupler substituted in the meta position by two amino groups, at least one of the amino groups being primary, and
washing said keratinous fibers with at least one detergent composition comprising at least one non-ionic surfactant chosen from alkylpolyglycoside surfactants and polyglycerolated surfactants.

31. The process according to claim 30, wherein said keratinous fibers are sensitized keratinous fibers.

* * * * *